United States Patent [19]

Lue

[11] Patent Number: 4,956,994

[45] Date of Patent: Sep. 18, 1990

[54] METHOD AND APPARATUS FOR TESTING THE CURING CHARACTERISTICS OF PLASTICS

[75] Inventor: Ching-Tai Lue, Dover, N.H.

[73] Assignee: Davidson Textron Inc., Dover, N.H.

[21] Appl. No.: 335,951

[22] Filed: Apr. 10, 1989

[51] Int. Cl.$^5$ ............................................. G01N 3/48
[52] U.S. Cl. ......................................................... 73/81
[58] Field of Search ................. 73/81, 82; 33/832–834, 33/836

[56] References Cited

U.S. PATENT DOCUMENTS

| | | | |
|---|---|---|---|
| 490,860 | 1/1893 | Snoeck | 33/836 |
| 1,232,782 | 7/1917 | Field | 73/81 |
| 2,509,692 | 5/1950 | Miller | 73/81 |
| 2,650,435 | 9/1953 | Kidd | 33/836 |
| 2,791,903 | 5/1957 | Lundstedt | 73/82 |
| 2,975,631 | 3/1961 | Hansen | 73/81 |
| 3,078,710 | 2/1963 | Palmer | 73/81 |
| 3,421,364 | 1/1969 | Moneypenny et al. | 73/82 |
| 4,565,089 | 1/1986 | Arciszewski et al. | 73/82 |

FOREIGN PATENT DOCUMENTS

| | | | |
|---|---|---|---|
| 2835038 | 2/1980 | Fed. Rep. of Germany | 73/81 |
| 2047411 | 11/1980 | United Kingdom | 73/81 |

Primary Examiner—Robert Raevis
Attorney, Agent, or Firm—John C. Evans

[57] ABSTRACT

A plunger of a known mass is held in a guide sleeve of a test device at a predetermined height over the sample of settable plastic material being tested. The plunger is gently released onto the sample without impact to apply a static force thereon similar to a "handgrip" pressure applied on a molded part during handling. The static pressure is applied on the sample released at selected times and places after reactive components of the sample are mixed for reaction to effect a series of indentations on the sample whose depths are measured and plotted as points on a depth versus time graph to define a cure curve of the sample. Curing rate is determined from the initial slope of the curve. Cure completion is determined where the curve levels off. A measure of the likelihood of handling damage is established by the portion of the indentations after a given time period.

6 Claims, 2 Drawing Sheets

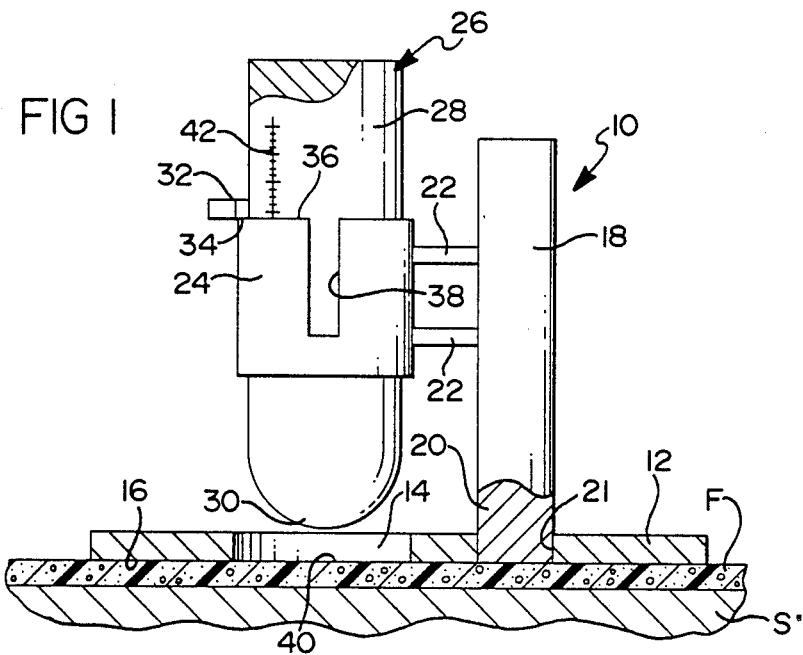
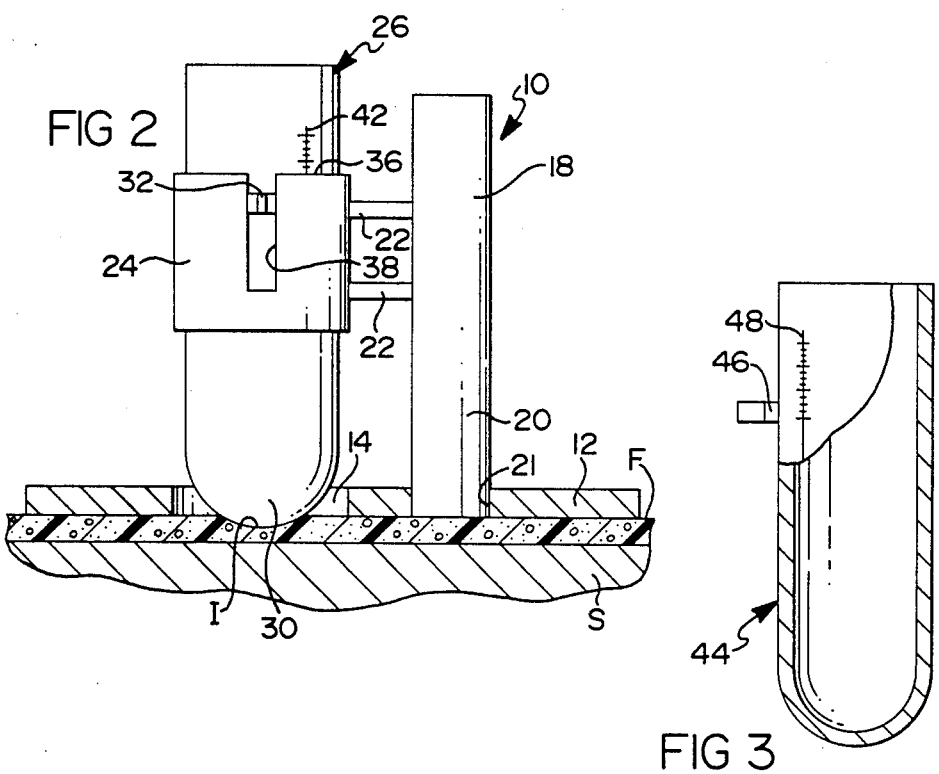

METHOD AND APPARATUS FOR TESTING THE CURING CHARACTERISTICS OF PLASTICS

This invention relates to a new and improved testing device for determining the curing characteristics of soft thermoset polymers as well as other plastics, and further relates to a new and improved method of testing these plastics to ascertain such characteristics.

In order to determine whether plastics such as polyurethane foam have been properly cured and are ready for demolding and handling for storage or shipment, gel time and tack free time in a cup-rise test have been used to characterize their cures. Prior cup-rise test methodology includes the steps of mixing constituent parts of thermoset polymers, e.g., isocyanate and polyol blends in the case of polyurethane foam; pouring the mixture into a test cup and thereafter observing gel time and tack free time. Gel time is the time required for the mixed chemicals to change from a liquid stage to a stringy stage. Tack free time is the time required to reach a tack free stage observed by touching the reacting chemicals with a tongue presser and determining when there is no longer a foam surface tackiness.

Gel time and tack free time, as measures for curing characteristics, are very subjective to the operator. It is rare that data from two laboratories agree with each other. Furthermore, these two measures are only two arbitrary points on the viscosity build-up profile. Further, there is no basis for using either measure of gel time or tack free time as criteria for judging when a part can be demolded without leaving finger impressions in the part. As a matter of fact, it is possible that a chemical reaction system having a shorter tack free time than another such system actually requires a longer demold time in production.

Existing methods for testing the curing characteristics of plastics include measurements of dielectric properties for almost any kind of thermoset plastics, BB test, and vibrating ball viscometer tests for polyurethane foam. The dielectric method measures the changes of mobilities (very small scale of motion) of the reacting molecules which decrease as the reaction proceeds. The BB test and vibrating ball test measure the changes of viscosity of the reacting molecules which increase as the reaction proceeds. To various degrees, they all offer some kind of "relative" measure for curing rate. However, none of these methods offers a "direct" measure of demoldability, i.e., whether the part can maintain its shape at the time of demolding and withstand the handgripping at demolding and subsequent handling.

With the above in mind, the present invention provides a new and improved static pressure test method and apparatus that is accurate and reliable for determining finger impression resistance of curable plastics such as soft and resilient thermoset polymers produced by different processes without resort to subjective testing techniques.

More particularly, the testing apparatus of the preferred embodiment of this invention is a portable unit and comprises a base for placement at any selected place directly on the plastic material being tested. The base has an access opening therethrough so that some of the material under the base is exposed for test purposes. A cylindrical guide sleeve is mounted to the base directly above the opening and receives a plunger of a large known mass which is operatively mounted therein so that it can be released gradually from a predetermined height above the material for applying a predetermined static load (pressure) on the sample being tested to effect an indentation therein similar to that produced by fingers applying handgrip pressure to a part during demolding. A suitable scale is provided on the plunger or guide sleeve that cooperates with a pointer or index on the other of the relatively slideable elements so that the depth of indentation or penetration of the plunger into the material can be ascertained. In the event that the memory of a resilient material is being measured, a measuring device in the shape of the plunger but having an optimally reduced mass is used to measure the depth of the same indentations after a predetermined time lapse.

The test method of this invention provides a direct and quantitative measure for determining the cure characteristics of a thermoset plastic material. The method determines susceptibility to permanent indentations by applying a static load on a sample at a time after mixing of the various components of the material at a first point thereon to effect a first indentation therein. The depth and time of the indentation are measured and recorded, then the given static load is applied to other points on said material at a selected different time from one another and from the time of initial mixing to effect a series of indentations separate from one another and from the first indentation. Each indentation is measured and recorded as to its depth and time of formation until the indentations being made are substantially constant in depth. The cure time for production of the material can then be ascertained from reading the time elapsed from the mixing to the first indentation of the series that has a depth which is substantially constant with the remainder of said indentations of the series. The rate of cure can be determined from the slope of the initial straight portion of the plotted curve tracing the points of indentation with the depth of indentation as one of the coordinates and the time after mixing as the other coordinate.

Recovery of resilient materials can be determined by plotting a second curve using a low mass measuring device in place of the indenting device to measure the recovered depth of each indentation after a given time lapse. If original indentations in the material show little recovery, the likelihood of handling damage such as permanent deformation of a plastics part on demolding is high, thereby advising the testor that rejection or further processing of the material is needed. A high recovery reading of the tested plastics (such as no permanent indentation) shows that there will be no permanent deformations when a part made from the plastics is demolded or handled. Consequently, a quantitative measure is available to determine if a given reaction process and the plastics produced thereby can be demolded and handled without leaving permanent impressions therein.

The method of the present invention also offers measures of the initial cure rate and the completion of cure of thermoset plastic material so that more detailed comparison can be made among different reactive chemical systems to form such thermoset plastic materials.

These and other features, objects and advantages of this invention will be more apparent from the following detailed description and drawings in which:

BRIEF DESCRIPTION OF THE DRAWINGS

FIG. 1 is a side view partly in section of a preferred embodiment of the invention as placed on a plastic being tested;

FIG. 2 is a view similar to the view of FIG. 1 but with a component thereof in a moved position.

FIG. 3 is a side view partly in section of a hollow low mass measuring device used in this invention.

DETAILED DESCRIPTION OF THE PREFERRED EMBODIMENT

Figure 4:
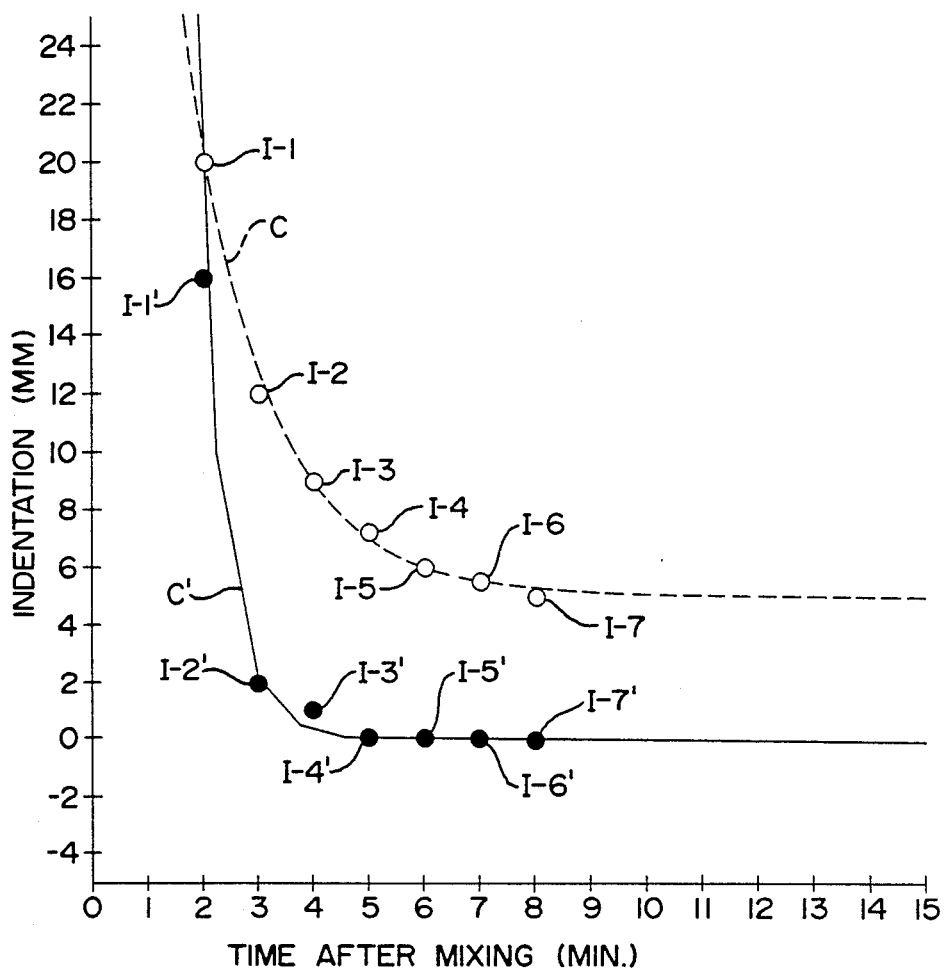
FIG. 4 is a Cartesian coordinate curve illustrating the curing characteristics of the hot set testing device and method of this invention.

Turning now in greater detail to the drawings, FIG. 1 shows a testing device 10 comprised of a base 12 made from flat stock which can have any suitable plan view configuration, annular or rectilinear, for example, with a circular opening 14 therethrough and with a planar bottom surface 16. The testing device is portable so that the base can be positioned directly on the upper surface of a hot settable plastic material such as polyurethane foam F being tested which in turn is supported on support S.

The present invention is suitable for use with any soft settable polymeric material. Examples of such materials include cast urethane, RIM urethanes, and polyurethane foam.

An elongated upright 18, cylindrical in cross-section has its lower end press fitted at 20 into an opening 21 in the base 12. Mounted to the upright 18 by connector 22 is a cylindrical retainer and guide sleeve 24 that slideably receives a plunger 26 of a predetermined mass which, in the preferred embodiment, is formed by a solid cylindrical body 28 of steel having a flat upper end and a rounded bullet nose lower end 30 for contacting and indenting the plastics undergoing test. A keeper 32 is secured to body 28 of the plunger and extends radially therefrom as shown in FIG. 1. The lower surface 34 of keeper 32 is flat finished for sliding contact with the flat finished upper surface 36 of the retainer and guide sleeve 24. With this construction, the plunger is held in the FIG. 1 position at a predetermined distance above the polyurethane foam sample F. The radial dimension of keeper 34 is sufficiently long so that it can be grasped as a handle with one's fingers and turned into alignment with the vertical slot or track 38 in the sleeve that is dimensioned to allow the turned body of the plunger to fall without interference into contact with the foam F through the base opening 14. A vertical scale 42 inscribed on the periphery of the plunger is read by utilizing the upper surface 36 of the retainer and guide sleeve 24 as an index which allows an accurate readout of the extent that the plunger penetrates into the plastic foam F during cure testing.

In addition to the solid high mass plunger 26 of FIG. 3, this invention may advantageously use a special measuring device 44 which has the same dimensions and shape as the plunger 26 so that it operatively fits in the sleeve 24 in place of the plunger 28. The measuring device 44 also has a keeper 46 corresponding to keeper 32 and a scale 48 corresponding to scale 42 which is read by using the upper surface 36 of the sleeve 24 as an index. The measuring device 44 is a hollow aluminum shell with optimal minimum weight so that when the scale is manually lowered into an indentation in the plastic material previously made by plunger 26 to measure the indentation depth, the plastic material will not be deflected by the measuring device to give an accurate reading.

After the polyurethane foam F has been processed by the mixing of its reactive component materials and is being cured, the testing device 10 can be placed at any selected position on the upper surface of the test sample as shown in FIG. 1. At a specific time, two minutes for example, after the mixing is completed, the plunger 26 is manually turned from its FIG. 1 position so that keeper 32 aligns with slot 38. The plunger 26 is then free to slide within the guide sleeve 24. The lower end 30 is gently engaged with the foam such that no significant impact force is applied to the molded part sample.

Since the plunger 26 is gently released, it gradually sits on the surface 40 of the foam F to impose a predetermined static pressure on the foam which, in turn, impresses an indentation I therein.

The predetermined pressure which is determined by the plunger weight and contact area is selected to be similar to the pressure applied on the part by finger contact due to handling at demold.

The depth of the initial indentation is measured from the scale 42 and the first indentation is plotted as point I-1 on the graph of FIG. 4. The plunger is moved back to the FIG. 1 position and the testing device is then manually placed on the foam sample F at any other desired position. At three minutes after mixing, or other selected time, the plunger is again released to make a second indentation with the same known force. The second indentation is plotted a point I-2 on the FIG. 4 graph. The same procedure is followed at different locations on the foam sample F and each indentation I-3, I-4, I-5, I-6, and I-7 is sequentially plotted on the graph as points which define the dashed line cure curve C. The completion of cure can be determined from the point where the curve starts to level off. For example, the point I-5 is a point at which the curve C is leveling off and would be determining of cure completion. The curing rate can be determined from the initial slope of curve C.

Using the light weight measuring device 44 instead of the plunger 26 which might deflect the foam and give an inaccurate reading, the indentations are again measured for depth at 24 hours after the first measures and plotted on the FIG. 4 graph as point I-1', I-2', I-3', I-4', I-5', I-6', and I-7', to correspond to points I-1 through I-7 as illustrated. The solid permanent indentation curve C' is then traced from the points. Indentation points I-1 to I-3 representing the first three indentations show permanent deformation to indicate that there would be damage, i.e. permanent deformation, if demolded after one, two or three minutes. Points I-4', through I-5', show that there is no measurable permanent indentations so that the parts can be demolded after five minutes after completion of the mixing and injected into a reaction mold without risk of any handling damage.

The preferred embodiments of this invention have been shown and described to illustrate the invention set forth in the following claims.

What is claimed is:

1. A device for testing the curing characteristics of a test sample of curable thermosetting polymer material comprising:
   a base adapted to be placed on a surface of said test sample of curable thermosetting polymer material during curing thereof; said base having an opening therethrough;

first support means affixed to said base and extending upwardly therefrom;

second support means including a guide sleeve affixed to said first support means and extending over said test sample and disposed at a predetermined distance therefrom;

a plunger slidably mounted within said guide sleeve, coacting means on said plunger and said guide sleeve for locating said plunger above said base opening and spaced from the surface of the test sample by supporting said plunger on said guide sleeve for subsequently positioning said plunger in non-impact contact with the surface of said test sample on which said base is supported to effect a finger contact pressure on the plastic material to form a first indentation in the surface of the test sample; said coacting means operable to reposition said plunger on said guide sleeve as said base is moved with respect to the surface of the test sample for aligning the plunger and said base opening with the test sample for subsequent non-impact contact with the surface of the test sample for producing a series of indentations in the surface of the test sample during a cure period.

2. The device defined in claim 1 above wherein said coacting means is defined by a guide member extending from a side of said plunger and wherein said second support means is defined by a cylindrical guide tube having a slot therein to form a track for said guide member.

3. The device defined in claim 1 and further including a scale on said plunger alignable with said upper end surface of said guide sleeve to indicate the amount of travel of said plunger into the upper surface of the test sample being tested.

4. The device of claim 1, further comprising a hollow light weight plunger of a predetermined mass operatively mounted by said guide sleeve in alignment with said base opening; said plunger having a rounded bullet configured end thereon with a width less than the width of said base opening;

said coacting means including a upper end surface on said guide sleeve and a guide member on said hollow light weight plunger supported on said upper end surface for locating said plunger above said base opening; and said coacting means further including a slot formed in said guide sleeve for receiving said guide member for vertical reciprocation with respect to said guide sleeve for releasing said hollow light weight plunger from support by said second support means for handheld movement relative thereto whereby said plunger will travel through said base opening without impact loading the surface of said test sample to measure a series of indentations in the surface of said test sample during a cure period.

5. A method for determining the curing characteristics of a test sample of a settable polymer material within a selected time period subsequent to the manufacture of said material from mixable components comprising the steps of:

providing a device for applying a non-impact load on a surface of a test sample made from said material including a guide sleeve, a plunger slidably supported in the guide sleeve and coacting means for supporting the plunger on the top of the guide sleeve and for hand releasing the plunger for movement against the upper surface of the test sample to emulate finger pressure thereon;

mixing said mixable components to form a test sample of uncured polymer material having an upper surface;

applying a given non-impact load to a first point on the upper surface of said test sample of uncured polymer material with the plunger to effect a first indentation in the upper surface of the material as it cures;

applying said given non-impact load to a second point on the upper surface of said polymer material by hand releasing the plunger to a second point on the upper surface at a selected time after said first indentation has been made to effect a second indentation in the upper surface of said material;

measuring and recording the depth of the second indentation, subsequently hand releasing the plunger for applying said given non-impact load to a series of other points on the upper surface of said polymer material each at a different selected time after said first indentation has been made to effect a series of other indentations in said material until the depth of said other indentations in said material until the depth of said other indentations is substantially constant to reflect the cure point of the material, and correlating the cure point of said material with the time elapsed from said mixing of uncured polymer to the production of indentations with the depths thereof of substantially constant value.

6. The method defined in claim 5 and further comprising the steps of remeasuring the depths of the indentations subsequent to a predetermined time period after the first indentations were made and determining the amount of recovery of said plastic material so that the liability from demolding of mixable components can be subsequently determined.

* * * * *